United States Patent
Zeng et al.

(10) Patent No.: US 10,304,217 B2
(45) Date of Patent: May 28, 2019

(54) METHOD AND SYSTEM FOR GENERATING IMAGE USING FILTERED BACKPROJECTION WITH NOISE WEIGHTING AND OR PRIOR IN

(75) Inventors: Gengsheng L. Zeng, Salt Lake City, UT (US); Alexander Zamyatin, Hawthorn Woods, IL (US)

(73) Assignees: TOSHIBA MEDICAL SYSTEMS CORPORATION (JP); UNIVERSITY OF UTAH REASEARCH FOUNDATION, Salt Lake City, UT (US)

( * ) Notice: Subject to any disclaimer, the term of this patent is extended or adjusted under 35 U.S.C. 154(b) by 714 days.

(21) Appl. No.: 13/561,674

(22) Filed: Jul. 30, 2012

(65) Prior Publication Data

US 2014/0029819 A1 Jan. 30, 2014

(51) Int. Cl.
*A61B 6/00* (2006.01)
*A61B 6/03* (2006.01)
*G06T 11/00* (2006.01)
*G06K 9/00* (2006.01)

(52) U.S. Cl.
CPC .......... *G06T 11/003* (2013.01); *G06T 11/006* (2013.01); *A61B 6/032* (2013.01); *A61B 6/5258* (2013.01); *G06T 2211/421* (2013.01); *G06T 2211/424* (2013.01)

(58) Field of Classification Search
None
See application file for complete search history.

(56) References Cited

U.S. PATENT DOCUMENTS

| | | | | |
|---|---|---|---|---|
| 4,991,093 | A * | 2/1991 | Roberge | G01N 23/046 382/131 |
| 6,438,195 | B1 * | 8/2002 | Hsieh | 378/4 |
| 7,653,229 | B2 * | 1/2010 | Kaufhold et al. | 382/131 |
| 8,135,186 | B2 * | 3/2012 | Bouman | G06T 11/006 378/19 |
| 9,053,538 | B2 * | 6/2015 | Takahashi | G06T 5/002 378/87 |

(Continued)

FOREIGN PATENT DOCUMENTS

| | | |
|---|---|---|
| CN | 101877124 A | 11/2010 |
| CN | 102596040 A | 7/2012 |

(Continued)

OTHER PUBLICATIONS

La Rivière et al., "Reduction of Noise-Induced Streak Artifacts in X-Ray Computed Tomography Through Spline-Based Penalized-Likelihood Sinogram Smoothing", IEEE Transactions on Medical Imaging, vol. 24 No. 1, Jan. 2005, pp. 105-111.*

(Continued)

*Primary Examiner* — Mathew C Bella
*Assistant Examiner* — Jose Torres
(74) *Attorney, Agent, or Firm* — Kenichiro Yoshida

(57) ABSTRACT

An image is reconstructed based upon a filtered backprojection (FBP) technique using a reconstruction filter which is customized or shaped by parameters including a weight value that is determined for weighing projection data according to a predetermined noise model. The weight value is determined based upon rays or views in the projection data. A regularization term is also combined with the noise-weighted FBP.

22 Claims, 13 Drawing Sheets

(56) References Cited

U.S. PATENT DOCUMENTS

| | | | |
|---|---|---|---|
| 2003/0076988 A1* | 4/2003 | Liang et al. | 382/131 |
| 2003/0219152 A1* | 11/2003 | August | G06T 11/005 382/131 |
| 2004/0114728 A1* | 6/2004 | Schlegel et al. | 378/901 |
| 2004/0258194 A1* | 12/2004 | Chen et al. | 378/4 |
| 2005/0113681 A1* | 5/2005 | DeFreitas | A61B 6/502 600/426 |
| 2006/0109952 A1* | 5/2006 | Chen | G06T 11/006 378/4 |
| 2007/0198203 A1* | 8/2007 | Kimura | G06T 5/002 702/85 |
| 2008/0049891 A1* | 2/2008 | Yin | G06T 11/006 378/9 |
| 2008/0118128 A1* | 5/2008 | Toth | 382/131 |
| 2008/0135789 A1* | 6/2008 | Du | A61B 6/032 250/580 |
| 2008/0304731 A1* | 12/2008 | Kimura | G06T 5/002 382/131 |
| 2009/0161935 A1* | 6/2009 | Bruder | A61B 6/481 382/131 |
| 2010/0034356 A1* | 2/2010 | Hayashida | H04L 67/12 378/98 |
| 2011/0052030 A1* | 3/2011 | Bruder et al. | 382/131 |
| 2011/0058724 A1* | 3/2011 | Claus | 382/132 |
| 2011/0150305 A1* | 6/2011 | Zeng et al. | 382/131 |
| 2012/0045108 A1* | 2/2012 | Shechter | 382/131 |
| 2012/0294414 A1* | 11/2012 | Koehler | 378/16 |
| 2013/0004041 A1* | 1/2013 | Yang | G06K 9/40 382/131 |
| 2013/0101194 A1* | 4/2013 | Zeng | 382/131 |
| 2013/0202079 A1* | 8/2013 | Yu | A61B 6/5258 378/19 |
| 2013/0202172 A1* | 8/2013 | Weitzel | G06T 11/008 382/131 |
| 2013/0251286 A1* | 9/2013 | Brendel et al. | 382/275 |
| 2014/0219417 A1* | 8/2014 | Batenburg et al. | 378/19 |

FOREIGN PATENT DOCUMENTS

| | | |
|---|---|---|
| JP | 2006025868 A | 2/2006 |
| JP | 2012-070814 A | 4/2012 |
| KR | 100825048 B1 | 4/2008 |
| WO | 2012073167 A1 | 6/2012 |

OTHER PUBLICATIONS

Zamyatin et al., "Streak Artifact Reduction in Low Dose Computed Tomography", Nuclear Science Symposium and Medical Imaging Conference (NSS/MIC), 2011 IEEE, pp. 4150-4151.*

Wang et al., "Noise Reduction for Low-Dose Single-Slice Helical CT Sinograms", IEEE Transactions on Nuclear Science, vol. 53 Issue 3, Jun. 2006, pp. 1230-1237.*

Sauver et al., "Nonstationary filtering for removal of signal dependent noise in reconstructions from projections", 1989 International Conference on Acoustics, Speech, and Signal Processing, May 23-26, 1989, pp. 1476-1479.*

Feng et al., "An angular frequency dependent filter for PET reconstruction", 2001 IEEE Nuclear Science Symposium Conference Record, Nov. 4-10, 2001, pp. 1742-1745.*

Lyra et al., "Filtering in SPECT Image Reconstruction", International Journal of Biomedical Imaging, vol. 2011, pp. 1-14.*

Shtok et al., "Adaptive filtered-back-projection for computed tomography", IEEE 25th Convention of Electrical and Electronics Engineers in Israel, Dec. 3-5, 2008, pp. 528-532.*

Suzuki et al., "Comparison between an image reconstruction method of filtering backprojection and the filtered backprojection method", Applied Optics, vol. 27 Issue 14, Jul. 15, 1988, pp. 2867-2870.*

International Search Report (in English) corresponding to International Application No. PCT/JP2013/070659 dated Nov. 5, 2013.

Akifumi Fujita et al, "Evaluation of Ultra-low-dose Thoracic Multi-detector-row CT using Different Reconstruction Kernels and New Reconstruction Algorithms", Journal "Nippon ACTA Radiologica", Nov 25, 2003, p. 588-590, vol. 63 Issue No. 9, Japan Radiological Society, Kanagawa, Japan.

Gengsheng L. Zeng. "A filtered backprojection algorithm with characteristics of the iterative landweber algorithm," Medical Physics, Feb. 2012, vol. 39 (2), p. 603-607, vol. 39, American Association of Physicists in Medicine, College Park, MD, USA.

Omer Demirkaya, "Reduction of noise and image artifacts in computed tomography by nonlinear filtration of the projection images," Proceedings of SPIE, Feb. 2001, p. 917-923, vol. 4322, SPIE, Bellingham, WA, USA.

Gengsheng L. Zeng, "Filtered Backprojection Algorithm Can Outperform Iterative Maximum Likelihood Expectation-Maximization Algorithm," International Journal of Imaging Systems and Technology, Mar. 2012, p. 114-120, vol. 22, Wiley Periodicals, Inc., USA.

Hongbing Lu et al., "Analytical Noise Treatment for Low-Dose CT Projection Data by Penalized Weighted Least-Square Smoothing in the K-L Domain," Proceedings of SPIE, 2002, p. 146-152, vol. 4682, SPIE, Bellingham, WA, USA.

Ken Sauer et al., "Nonstationary Filtering of Transmission Tomograms in High Photon Counting Noise," IEEE Transactions on Medical Imaging, Sep. 1991, p. 445-452, vol. 10, IEEE, Iowa City, IA, USA.

Junmei Zhong et al., "Image Denoising Based on Multiscale Singularity Detection for Cone Beam CT Breast Imaging," IEEE Transactions on Medical Imaging, Jun. 2004, p. 696-703, vol. 23, IEEE, Iowa City, IA, USA.

Tianfang Li et al., "Nonlinear Sinogram Smoothing for Low-Dose X-Ray CT," IEEE Transactions on Nuclear Science, Oct. 2004, p. 2505-2513, vol. 51, IEEE, Albuquerque, NM, USA.

Patrick J. La Riviere et al., "Reduction of Noise-Induced Streak Artifacts in X-Ray Computed Tomography Through Spline-Based Penalized-Likelihood Sinogram Smoothing," IEEE Transactions on Medical Imaging, Jan. 2005, p. 105-111, vol. 24, Iowa City, IA, USA.

Jing Wang et al., "Penalized Weighted Least-Squares Approach to Sinogram Noise Reduction and Image Reconstruction for Low-Dose X-Ray Computed Tomography," IEEE Transactions on Medical Imaging, Oct. 2006, p. 1272-1283, vol. 25, Iowa City, IA, USA.

Marc Kachelriess et al., "Generalized multi-dimensional adaptive filtering for conventional and spiral single-slice, multi-slice, and cone-beam CT," Medical Physics, Apr. 2001, p. 475-490, vol. 28, American Association of Physicists in Medicine, College Park, MD, USA.

Patrick J. La Riviere et al., "Penalized-likelihood sinogram smoothing for low-dose CT," Medical Physics, Jun. 2005, p. 1676-1683, vol. 32, American Association of Physicists in Medicine, College Park, MD, USA.

Jiang Hsieh, "Adaptive streak artifact reduction in computed tomography resulting from excessive x-ray photon noise," Medical Physics, Nov. 1998, p. 2139-2147, vol. 25, American Association of Physicists in Medicine, College Park, MD, USA.

Gengsheng L. Zeng et al., "A filtered backprojection MAP algorithm with nonuniform sampling and noise modeling," Medical Physics, Apr. 2012, p. 2170-2178, vol. 39, American Association of Physicists in Medicine, College Park, MD, USA.

Chinese Office Action for Application 201380001535.4, dated Jan. 5, 2016.

Korean Notice of Allowance of Corresponding Application No. 10-2013-7031515 dated Nov. 20, 2015.

Extended European Search Report (in English) corresponding to European Application No. 13825580.7 dated Jul. 5, 2016.

Gengsheng L.Zeng and Alex Zamyatin, "Ray-by-Ray Noise Weighting in a Filtered Backprojection (FBP) Algorithm," 2012 IEEE Nuclear Science Symposium and Medical Imaging Conference Record (NSS/MIC) M09-10, (2012).

* cited by examiner

METHOD AND SYSTEM FOR GENERATING IMAGE USING FILTERED BACKPROJECTION WITH NOISE WEIGHTING AND OR PRIOR IN

FIELD OF THE INVENTION

The current invention is generally related to image processing method and system for processing projection data using a noise weighted filtered backprojection technique.

BACKGROUND OF THE INVENTION

The filtered backprojection (FBP) algorithm is generally simple and efficient and is used to reconstruct images in nuclear medicine, x-ray CT and MRI. The FBP algorithm has been the workhorse in X-ray CT and nuclear medicine image reconstruction thanks to its computational efficiency. Although FBP is efficient, it undesirably produces noisy images particularly from data acquired at a low dose of X-ray.

As a general trend, the FBP algorithm is gradually being replaced by iterative algorithms despite its use for several decades. The FBP algorithm undesirably generates images with noise. Furthermore, prior art indicates that the FBP algorithm is not capable of incorporating a noise model for reducing the noise level. In this regard, iterative algorithms optionally incorporate a projection noise model and produce less noisy images than the FBP algorithm. Yet, iterative algorithms generally require intense computation.

Despite the computational requirements, iterative algorithms advantageously produce noise-resolution balanced images using maximum a posteriori (MAP). In contrast, prior art indicates that the FBP algorithm is not capable of taking advantage of MAP or prior image information.

In view of the above discussed prior art issues, a practical solution is still desired for a method and a system in reconstructing an image using the FBP algorithm to substantially reduce noise in the image without losing computational efficiency.

DETAILED DESCRIPTION OF THE PREFERRED EMBODIMENT(S)

Figure 1:
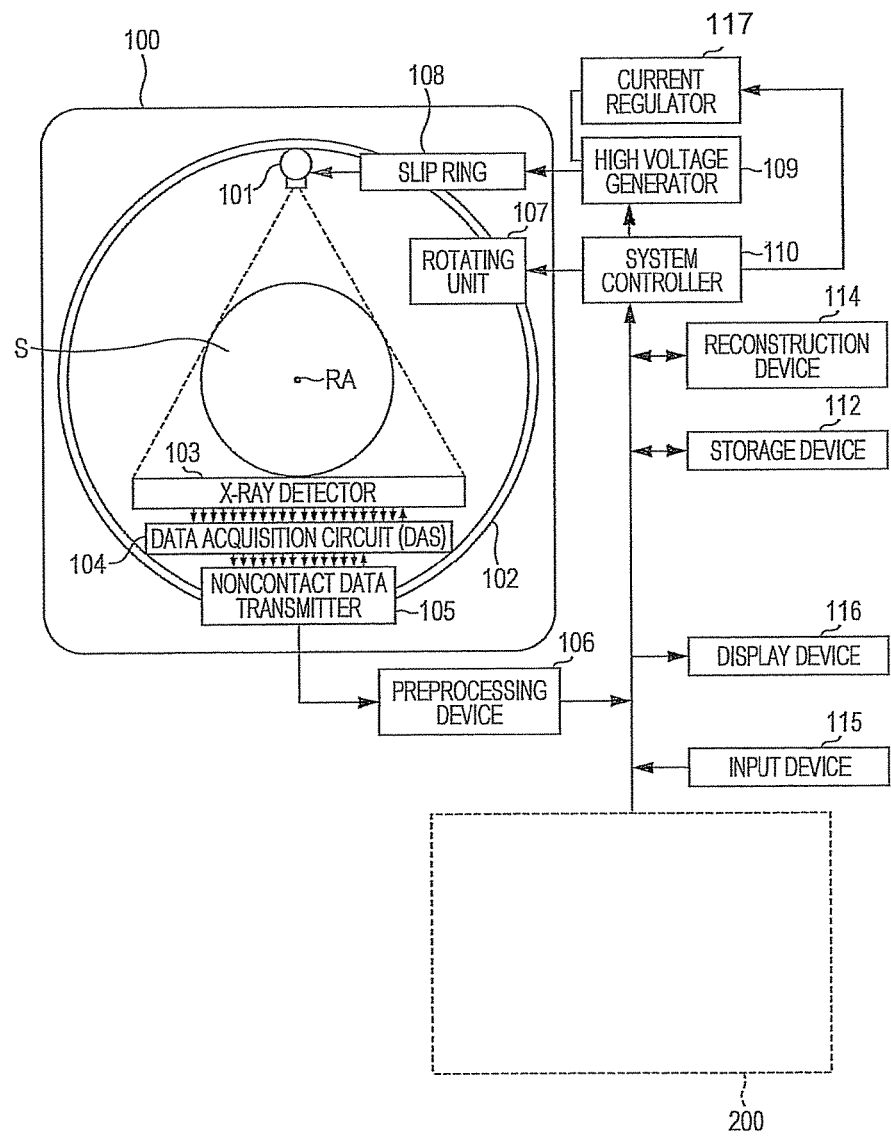
FIG. 1 is a diagram illustrating one embodiment of the multi-slice X-ray CT apparatus or scanner according to the current invention.

Referring now to the drawings, wherein like reference numerals designate corresponding structures throughout the views, and referring in particular to FIG. 1, a diagram illustrates one embodiment of the multi-slice X-ray CT apparatus or scanner according to the current invention including a gantry 100 and other devices or units. The gantry 100 is illustrated from a front view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which rotates around axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that applies a tube voltage to the X-ray tube 101 so that the X-ray tube 101 generates X ray. In one embodiment, the high voltage generator 109 is mounted on the frame 102. The X rays are emitted towards the subject S, whose cross sectional area is represented by a circle. The X-ray detector 103 is located at an opposite side from the X-ray tube 101 across the subject S for detecting the emitted X rays that have transmitted through the subject S.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR).

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116, current regulator 117 and the scan plan support apparatus 200. The scan plan support apparatus 200 includes a function for supporting an imaging technician to develop a scan plan.

According to one aspect of the current invention, one embodiment of the reconstruction device 114 reconstructs an image from the projection data that is stored in the storage device 112 based upon a filtered backprojection (FBP) technique with noise weighting. In another embodiment of the reconstruction device 114 reconstructs an image from the projection data based upon a filtered backprojection (FBP) technique with noise weighting and prior in such as a reference image. Either one of the above two embodiments of the reconstruction device 114 reconstructs an image from the projection data based upon a filtered backprojection (FBP) technique with an additional feature of emulating a specific iteration result at a predetermined number of iterations according to a predetermined iterative reconstruction algorithm.

The reconstruction device 114 is implemented in a combination of software and hardware and is not limited to a particular implementation. In the following description of the reconstruction device 114, the term, "unit" is inclusive of hardware and software. Furthermore, the concept of the reconstruction device 114 is applicable to other modalities including nuclear medicine and magnetic resonance imaging (MRI).

Figure 2:
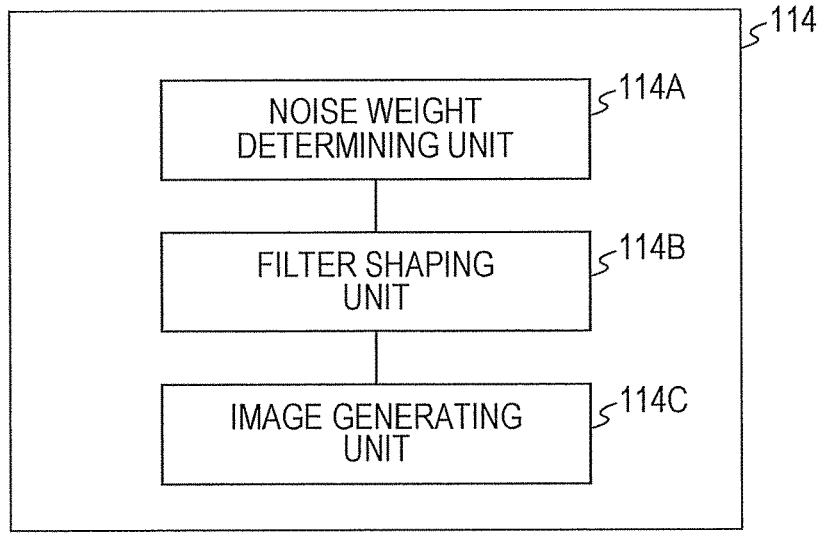
FIG. 2 is a diagram illustrating that the reconstruction device further includes units or components for reconstructing an image from the projection data according to the current invention.

Now referring to FIG. 2, the reconstruction device 114 further includes units or components for reconstructing an image from the projection data according to the current invention. One embodiment of the reconstruction device 114 includes a noise weight determining unit 114A for determining a weight value for weighing projection data at least according to a predetermined noise model, a filter shaping unit 114B, which is connected to the noise weight determining unit 114A for shaping at least one reconstruction filter based upon parameters including the weight value and an image generating unit 114C, which is connected to the filter shaping unit 114B for generating an image based upon the reconstruction filter. The implementation of the reconstruction device 114 is merely illustrative, and other embodiments according to the current invention are not limited to include these particular units, functions and or nomenclatures. Each of these units 114A, 114B and 114C will be further described in detail with respect to the features according to the current invention.

Figure 3:
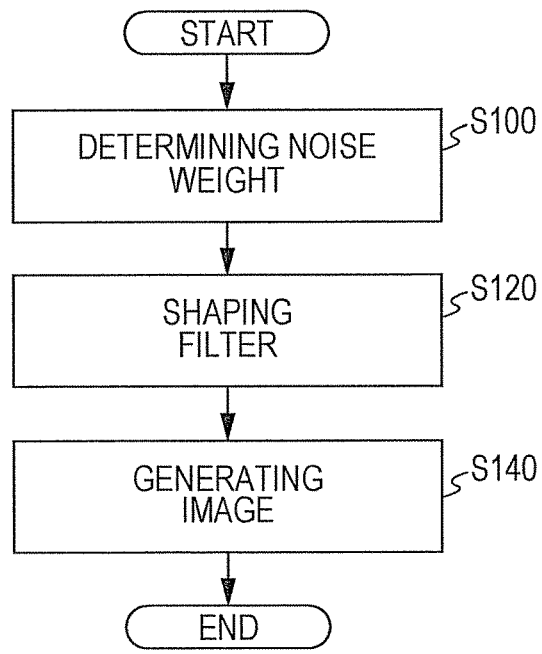
FIG. 3 is a flow chart illustrating acts, steps and or functions involved in one exemplary process of reconstructing an image according to the current invention.

Now referring to FIG. 3, a flow chart illustrates acts, steps and or functions involved in one exemplary process of reconstructing an image according to the current invention. These steps may be performed by one embodiment of the reconstruction device 114 according to the current invention. In a step S100, a weight value is determined for weighing projection data at least according to a predetermined noise model. A weight value is determined for a predetermined unit of projection data, and the data unit includes views and rays. In a step S120, at least one reconstruction filter is shaped or customized based upon certain parameters including the weight value as determined in the step S100. The parameters are not limited to the weight value while a plurality of the reconstruction filters is also optionally used for customization according to the current invention. Lastly, one process of reconstructing an image according to the current invention performs the generation of an image in a step S140 based upon the reconstruction filter as shaped in the step S120.

The step S120 shapes the filter based upon predetermined parameters. As described above, one exemplary parameter is noise variance in the projection data, but the parameters according to the current invention are not limited to the noise parameter. For example, the reconstruction filter is shaped based upon a system matrix. In further detail, the system matrix specifies non-uniform sampling of the projection data. Although the conventional FBP algorithm assumes that the object is uniformly sampled, one can use variable sampling strategies. For example, signal is sampled with a first angular interval in a certain angular range containing an important structure. In contrast, signal is sampled with a second angular interval that is larger than the first angular interval in another angular range outside the region of interest.

In another exemplary process of reconstructing an image according to the current invention, the step S100 is not necessarily performed and completed before the step S120 in determining the weight value for each of the predetermined data unit of projection data. In other words, the exemplary process of reconstructing an image optionally determines the weight value as the reconstruction filter is shaped. This on-the-fly weight value approach is useful for certain combined features of the process of reconstructing an image according to the current invention.

Still referring to FIG. 3, the image-generating step S140 performs a certain predetermined set of sub steps while applying the reconstruction filter as shaped in the step S120 according to the current invention. One exemplary process reconstructs an image by applying the customized filter to the projection data in frequency domain after Fourier transform in a predetermined FBP technique as will be further detailed. Another exemplary process reconstructs an image by applying the customized filter to the projection data in spatial domain as convolution in a predetermined FBP technique.

Figure 4:
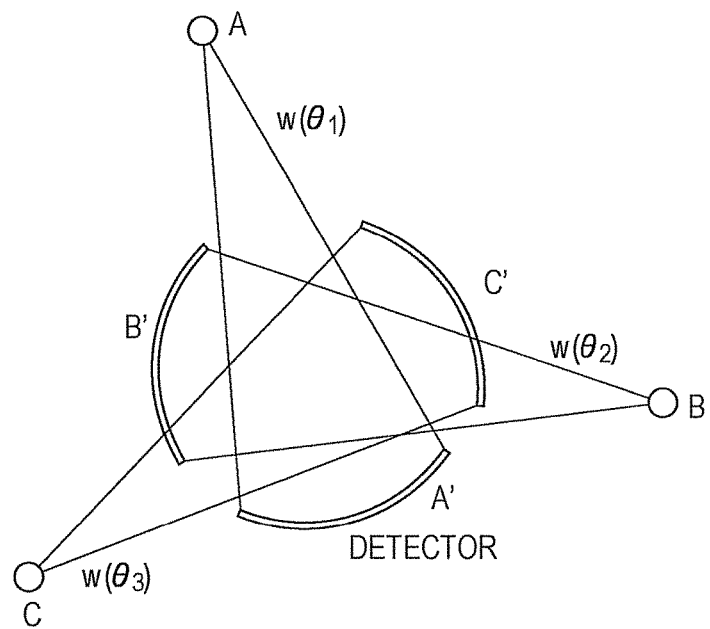
FIG. 4 is a diagram illustrating one exemplary scheme for determining view-by-view noise weight values in one exemplary process of reconstructing an image according to the current invention.

Now referring to FIG. 4, a diagram illustrates one exemplary scheme for determining view-by-view noise weight values in one exemplary process of reconstructing an image according to the current invention. In a view-wise weighting scheme, each view is generally assigned a weight value according to a predetermined function such as maximum or average noise variance in a particular view. The diagram illustrates an X-ray source at three positions A, B and C as well as a detector at the three corresponding positions at A', B' and C'. For example, when the X-ray source is at the position A, the detector is at the corresponding position A'. The projection data that is originally acquired at the detector at the position A' consists a view, and a weight value $w(\theta_1)$ is determined as a function of a view angle $\theta_1$ according to a predetermined weighting scheme for the view. As described above, the view weight value determination is performed and completed in advance of shaping a reconstruction filter in one exemplary process. The view weight value determination is determined as a reconstruction filter is shaped in another exemplary process.

The projection noise variance can be modeled using a view-based weighting scheme in embodiment according to the current invention. In general, a typical approach in image reconstruction while compensating for the noise influence is to minimize a noise variance weighted objective function:

$$\|P-AX\|_W^2 \qquad (1)$$

where A is the projection matrix, X is the image array written as a column vector, P is the projection array written as a column vector, and W is the noise weighting matrix which defines a weighted norm. An iterative Landweber algorithm is used to minimize this objective function as:

$$X^{(k+1)}=X^{(k)}+\alpha A^T W(P-AX^{(k)}) \qquad (2)$$

where $A^T$ is the backprojection matrix, $X^{(k)}$ is the estimated image at the kth iteration, and $\alpha>0$ is the step size. This recursive relation is re-written as a non-recursive expression as $$X^{(k)} = \alpha\left[\sum_{n=0}^{k-1}(I-\alpha A^T WA)^n\right]A^T WP \qquad (3)$$
$$= [I-(I-\alpha A^T WA)^k](A^T WA)^{-1}A^T WP.$$

Assuming that $(A^TWA)^{-1}=A^{-1}W^{-1}(A^T)^{-1}$ exists, Equation (3) is simplified as:

$$X^{(k)}=[I-(I-\alpha A^T WA)^k]A^{-1}P. \qquad (4)$$

The matrix expression (4) is equivalent to a noise weighted FBP algorithm and its filter function in the frequency domain is by $$H(\omega, \text{view}) = \left[1-\left(1-\alpha\frac{w(\text{view})}{|\omega|}\right)^k\right]|\omega|, \qquad (5)$$
$$H(0, \text{view}) = 0$$

where ω is the frequency variable, w(view) is a weight value or a noise related weighting factor at a particular view angle, α is a parameter emulating the step-size in an iterative algorithm, and k is a parameter emulating the iteration number in an iterative algorithm. This view-wise weighted FBP (denoted as vFBP) algorithm has a shift-invariant point response function (PRF).

In the above embodiment, the reconstruction filter is shaped to emulate a specific iteration result at a predetermined number of iterations as noted in k according to a predetermined iterative reconstruction algorithm. The above feature for emulating iteration in the reconstruction filter is not necessarily included in another embodiment for reconstructing an image from the projection data using the view-wise weighted FBP algorithm according to the current invention.

Figure 5:
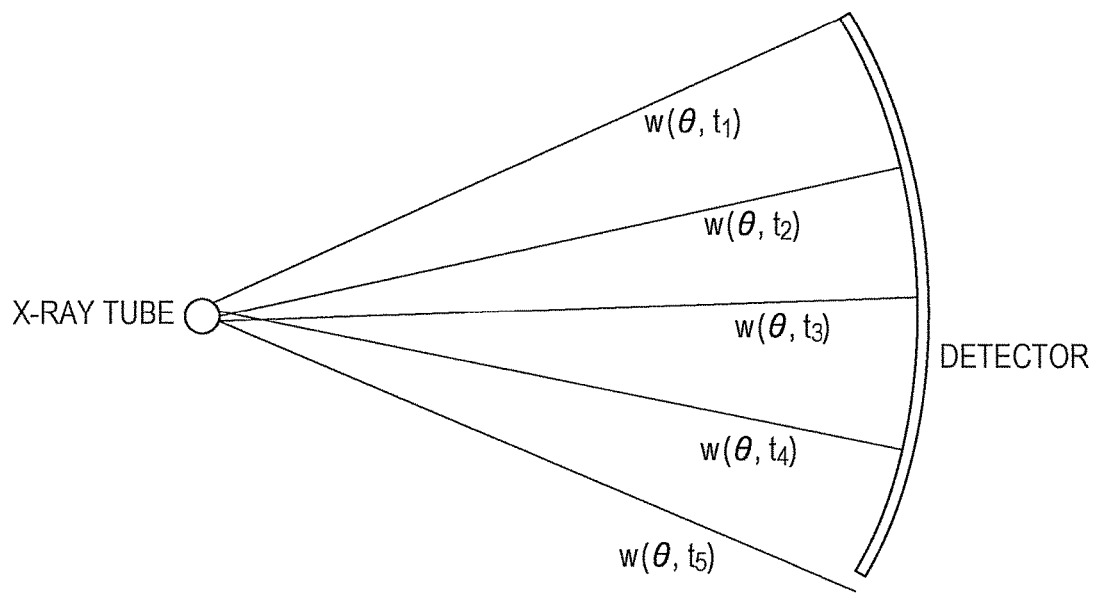
FIG. 5 is a diagram illustrating one exemplary scheme for determining ray-by-ray noise weight values in one exemplary process of reconstructing an image according to the current invention.

Now referring to FIG. 5, a diagram illustrates one exemplary scheme for determining ray-by-ray noise weight values in one exemplary process of reconstructing an image according to the current invention. In a ray-wise weighting scheme, each ray is generally assigned a weight value according to a predetermined function such as maximum or average noise variance in a particular view. The diagram illustrates an X-ray source at a predetermined position as well as a detector at a corresponding position. In the illustrated example, when rays are projected from the X-ray source, the projected rays reach the detector at the corresponding position. The projection data consists of a plurality of rays within a view angle at θ. For example, a weight value $w(\theta, t_1)$ is determined for a particular ray $t_1$ as a function of the view angle θ and according to a predetermined weighting scheme for the ray. As described above, the ray weight value determination is performed and completed in advance of shaping a reconstruction filter in one exemplary process. The ray weight value is determined as a reconstruction filter is shaped in another exemplary process.

As the requirement for a shift-invariant PRF is removed, a ray-by-ray weighting scheme is developed, and its frequency domain windowed ramp filter is obtained by modifying Equation (5) as follows:

$$H(\omega, \text{ray}) = \left[1-\left(1-\alpha\frac{w(\text{ray})}{|\omega|}\right)^k\right]|\omega|, \qquad (6)$$
$$H(0, \text{ray}) = 0$$

where a weight value or a weighting factor w(ray) is determined as a function of the noise variance of the associated projection ray. k is a parameter that specifies a predetermined number of iterations for emulating a specific iteration result at according to a predetermined iterative reconstruction algorithm. Let the inverse Fourier transform of H (ω, ray) be h(t,ray); then h(t,ray) is the spatial-domain kernel of the filter. Let p(r, θ) be the projection at view θ and ray r, and q(r, θ) be the filtered projection. Then q(r, θ) is defined by the following integral:

$$q(r, \theta) = \int_{-\infty}^{\infty} p(t, \theta)h(r-t, r)dt \qquad (7)$$

which is not a convolution, because the kernel h(t,r) depends on r. If the filtering procedure is implemented in the spatial domain as Equation (7), the calculation cost is the same as convolution. The backprojection step in this new rFBP algorithm is the same as that in the conventional FBP algorithm. Therefore, this new rFBP algorithm is computationally efficient. On the other hand, the image domain filtering is alternatively implemented in the 2D Fourier domain with a transfer function as will be later explained in a specific implementation for the ray-by-ray noise weighted FBP-MAP (rFBP-MAP) algorithm.

A popular approach to assign the weighting factor is to let w(ray) be the reciprocal of the noise variance of the ray measurement. This approach is justified by using the likelihood function (i.e., the joint probability density function) as the objective function for an optimization problem. If we use the philosophy that we should trust the less noisy measurements more than noisier measurements, we have more freedom to assign the weighting factors as long as a larger w(ray) is assigned to a less noisy measurement and a smaller w(ray) is assigned to a noisier measurement.

The easiest and most efficient way to implement the proposed rFBP algorithm is to use Equation (7) to filter the projections in the spatial domain. Currently, we do not have an analytical expression for the integration kernel h(t,r). An alternative way to calculate q(r, θ) for each view θ is to implement Equation (7) in the frequency domain as follows:

Step 1: Find the 1D Fourier transform of p(r, θ) with respect to r, obtaining P(ω,θ)

Step 2.a: For each ray "ray," assign a weighting factor w(ray) and form a frequency domain transfer function as expressed in Equation (6). In implementation, ω is the frequency index and takes the integer.

Step 2.b: Find the product: $Q_{ray}(\omega,\theta)=P(\omega,\theta)H(\omega, ray)$.

Step 2.c: Find the 1D inverse Fourier transform of $Q_{ray}$ (ω, θ) with respect to ω, obtaining q(ray, θ).

In the above exemplary implementation, Step 1 processes all r's in a row of each view while Steps 2.a through 2.c process only one ray at a time. In the view-by-view weighted FBP (vFBP) algorithm, a single weight value or weighting factor w(view) is assigned to all projection rays in a view. In contrast, the ray-by-ray weighted FBP (rFBP) algorithm, a distinct weight value or weighting factor w(ray) is assigned to each of the projection rays in a view. As a result, the noise-weighting scheme is more accurate in the ray-by-ray weighted FBP (rFBP) algorithm than in the view-by-view weighted FBP (vFBP) algorithm.

As described above with respect to the view-by-view weighted FBP (vFBP) algorithm and the ray-by-ray weighted FBP (rFBP) algorithm, embodiments shape at least one reconstruction filter based upon parameters including the weight value before generating an image according to the current invention. Furthermore, in the above embodiments, the reconstruction filter is shaped to emulate a specific iteration result at a predetermined number of iterations as noted in k according to a predetermined iterative reconstruction algorithm. The above feature for emulating iteration in the reconstruction filter is not necessarily included in another embodiment for reconstructing an image from the projection data using the view-wise or ray-wise weighted FBP algorithms according to the current invention.

Subsequently, embodiments perform certain steps for generating an image based upon the reconstruction filter that has been shaped or customized according to the current invention. In general, noise reduction in image reconstruction is based on the concept that image reconstruction especially in the backprojection is a summation procedure, and proper weighting of the projection data substantially reduces the variance of the backprojection.

Figure 6A:
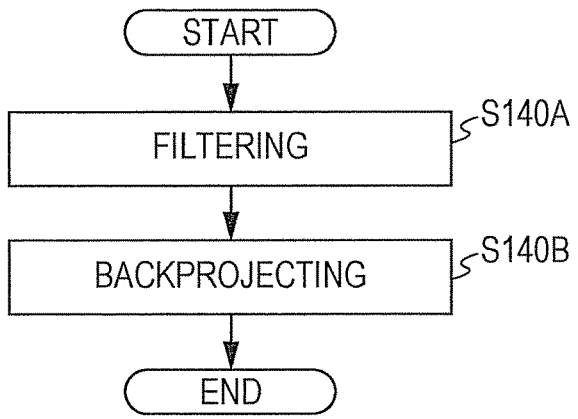
FIG. 6A is a flow chart illustrating an exemplary process involving additional steps for generating an image based upon the previously customized reconstruction filter according to the current invention.

Now referring to FIG. 6A, a flow chart illustrates an exemplary process involving additional steps for generating an image based upon the previously customized reconstruction filter according to the current invention. Assuming that the FBP algorithm performs the tasks on projection data, the reconstruction filter is applied to the projection data before backprojection is performed. Prior to a step S140A, the reconstruction filter has been already shaped or customized based upon parameters including noise weight values. In the step S140A, the customized reconstruction filter is applied to the projection data. Assuming that the projection data has undergone Fourier transform before the step S140A, the filtered projection data undergoes inverse Fourier transform before the step S140B. In the step S140B, the filtered projection data is now backprojected to render an image.

Figure 6B:
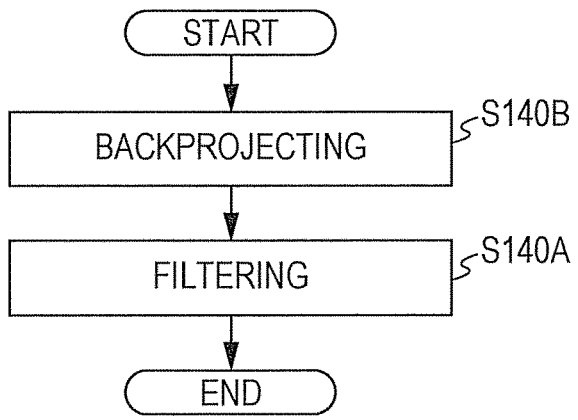
FIG. 6B is a flow chart illustrating an exemplary process involving additional steps for generating an image based upon the previously customized reconstruction filter according to the current invention.

Now referring to FIG. 6B, a flow chart illustrates an exemplary process involving additional steps for generating an image based upon the previously customized reconstruction filter according to the current invention. Assuming that the FBP algorithm performs the tasks on projection data, the reconstruction filter is applied to projection data after backprojection is performed. Also, assuming that the projection data has undergone Fourier transform before the step S140B, the projection data undergoes inverse Fourier transform before the step S140B. In the step S140B, the projection data is initially backprojected to render an image. The customized reconstruction filter is applied to the backprojected data. Prior to a step S140A, the reconstruction filter has been already shaped or customized based upon parameters including noise weight values. In the step S140A, the customized reconstruction filter is applied to the projection data.

Figure 7:
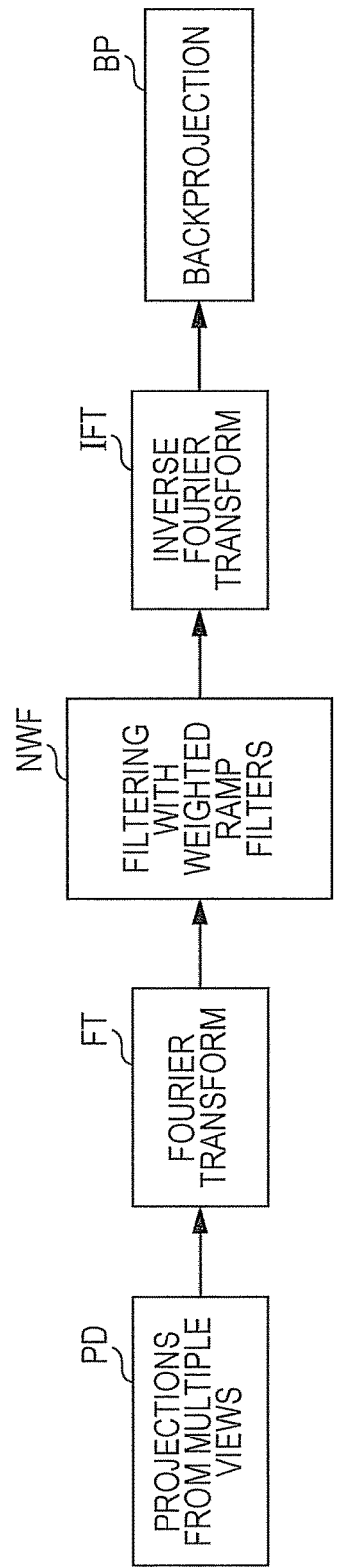
FIG. 7 is a diagram illustrating a general flow of reconstructing an image using a noise weighted ramp filter in a predetermined FBP algorithm in one embodiment according to the current invention.

Now referring to FIG. 7, a diagram illustrates a general flow of reconstructing an image using a noise weighted ramp filter in a predetermined FBP algorithm in one embodiment according to the current invention. In general, this embodiment assumes the noise weighted filtering takes place in the Fourier domain before backprojection to render an image. In this embodiment, projection data PD is provided from multiple views for reconstructing an image according to the current invention. The projection data PD is processed as views or optionally as rays in the embodiment. The projection data PD undergoes Fourier transform FT so that the transformed data is in the Fourier domain or frequency domain. A ramp filter is shaped and customized to a weighted ramp filter WF according to a set of predetermined parameters including a noise weight value. In certain embodiments, a plurality of the ramp filters is customized to be multiple weighted ramp filters WFs. In addition, the parameters are not limited to a noise weight parameter and optionally include other predetermined parameters. In this exemplary embodiment, the transformed projection data is filtered according to a noise weighted ramp filter NWF in the predetermined FBP algorithm. Finally, the filtered data in the frequency domain undergoes inverse Fourier transform IFT so that the projection data is backprojected in the spatial domain in backprojection BP. In a second embodiment, another noise weighted ramp filter NWF2 is optionally applied to the backprojected image in lieu of applying the noise weighted ramp filter NWF to the transformed data in the frequency domain. In the second embodiment, the noise weighted ramp filter NWF2 to be applied to an image is different in implementation from the noise weighted ramp filter NWF to be applied to the transformed data.

In one embodiment, the backprojection BP normalizes the above described varying angular sampling using a weighting function during the image generation. For example, signal is sampled with a first angular interval in a certain angular range containing an important structure. In contrast, signal is sampled with a second angular interval that is larger than the first angular interval in another angular range outside the region of interest. The backprojection BP is an integral over the sampling angle, and the angular sampling density compensation is achieved by using a normalization factor in the backprojection integral, which is essentially a Jacobian factor. Mathematically, a backprojection image is expressed as:

$$b(x, y) = \int_0^\pi p(t, \theta)\Big|_{t=x\cos\theta+y\sin\theta} d\theta \tag{8}$$

where p is raw projection at angle θ if the algorithm requires the raw projections be backprojected first. Alternatively, p is optionally the filtered projection at angle θ if an FBP algorithm is used, and t indicates the detector bin location. A simple discrete implementation of Equation (8) is given as $$b(i, j) = \frac{\pi}{M} \sum_{m=1}^{M} p(n, m) \Big|_{n=INT[x\cos\theta + y\sin\theta]} \quad (9)$$

where n is the detector location index, m is the projection angle index, M is the total number of views at which projections are acquired, and "INT" is used to indicate the nearest neighbor interpolation. In fact, a typical implementation does not use an "INT" function, but uses linear interpolation between two neighboring detector bins.

For the purposes of illustration, using the simple implementation as expressed in Equation (9), for the not uniform angular sampling, it obeys a density function d(0), which is the number of views per unit angle. For example, if the sampling interval is 1° for $0<\theta<\pi/4$ and 3° for $\pi/4<\theta<\pi$, then the density function is $$d(\theta) = \begin{cases} 1 & \text{for } 0 \le \theta < \pi/4 \\ 1/3 & \text{for } \pi/4 \le \theta < \pi \end{cases} \quad (10)$$

and the backprojection (9) can be modified as $$b(i, j) = \left(\pi \Big/ \sum_{m=1}^{M} \frac{d(1)}{d(m)}\right) \sum_{m=1}^{M} \frac{d(1)}{d(m)} p(n, m) \Big|_{n=INT[x\cos\theta + y\sin\theta]} \quad (11)$$

Here, the sampling density function is a function of the angle index in. instead of the actual angle θ.

Figure 8:
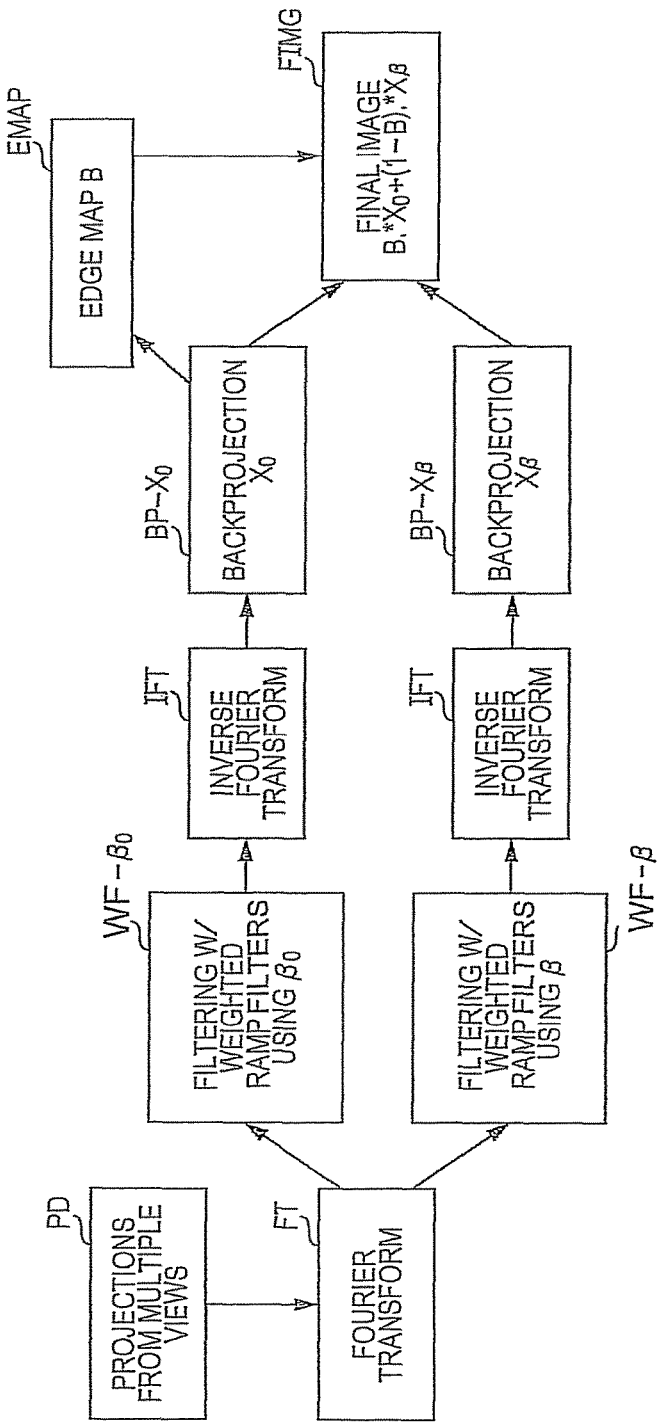
FIG. 8 is a diagram illustrating a general flow of reconstructing an image using a pair of noise weighted ramp filters in a predetermined Edge-preserving FBP-MAP algorithm in one embodiment according to the current invention.

Now referring to FIG. 8, a diagram illustrates a general flow of reconstructing an image using a pair of noise weighted ramp filters in a predetermined Edge-preserving FBP-MAP algorithm in one embodiment according to the current invention. In general, this embodiment assumes the noise weighted filtering takes place in the Fourier domain before backprojecting a pair of projection data to render images. Finally, the two images are combined to form a final image.

Still referring to FIG. 8, in this embodiment, projection data PD is provided from multiple views for reconstructing an image according to the current invention. The projection data PD is processed as views or optionally as rays in the embodiment. The projection data PD undergoes Fourier transform FT so that a pair of the transformed data is in the Fourier domain or frequency domain. A pair of ramp filters is separately shaped and customized to weighted ramp filters WF-$\beta_0$ and WF-$\beta$ according to a set of predetermined parameters including a noise weight value. In the embodiments, the ramp filters is additionally customized by regularization, and the filter is thus function of a value $\beta$. In general, the larger the value $\beta$, the more smoothing of the image takes place. For example, the $\beta$ value is selected to be zero for no smoothing or blurring. In this exemplary embodiment, the pair of the transformed projection data is respectively filtered by the noise weighted and regularized ramp filters WF-$\beta_0$ and WF-$\beta$ in the predetermined FBP algorithm. Subsequently, the pair of the filtered data in the frequency domain undergoes inverse Fourier transform IFT so that a pair of the projection data is backprojected in the spatial domain to render two images $X_0$ and $X_\beta$. The backprojected image $X_0$ with zero or minimal smoothing is optionally used for extracting edge map information B in an edge map EMAP that has been previously prepared. The minimally smoothed image $X_0$, the filtered image $X_\beta$ and the extracted edge information are combined to form a final image FIMG according to a certain rule.

In one exemplary embodiment as illustrated in FIG. 8, the edges are preserved during de-noising using a Bayesian regularization term in the objective function (12), where the penalty function g(X) measures a jump in an image pixel value relative to its neighbors.

$$F = \|P - AX\|_W^2 + \beta g(X) \quad (12)$$

where in the context of tomography, A in (1) is the projection matrix, X is the image array written as a column vector, P is the projection array written as a column vector, W is a diagonal matrix consisting of the weighting factors for each projection, and b is a relative weighting factor that adjusts the importance of the Bayesian term g(X) relative to the fidelity team $\|P-AX\|_W^2$.

In smoothing the image, the penalty g(X) is a quadratic function of a jump, and the jump is calculated as the difference between the value of the pixel of interest and the average value of its neighbors. A large jump corresponds to a large penalty, and this penalty function leads to a smooth image.

To suppress the image noise without smoothing out the edges too much, the penalty function g(X) should have different characteristics for edges and for non-edge regions. A common penalty function with such ability is the Huber function, which has a threshold value. If the jump is smaller than the threshold and the jump is classified as noise, the Huber function is quadratic and enforces smoothing. If the jump is larger than the threshold and the jump is classified as an edge, the Huber function is linear and lighter smoothing is suggested.

Another popular prior that encourages a piece-wise constant image is the TV (total-variation) measure. For a discrete one-dimensional function, g(x), the gradient of the TV measure of g(x) takes only three values: a positive value if g(x) is greater than its left and right neighbors; a negative value if g(x) is smaller than its left and right neighbors; 0 if g(x) is between its left and right neighbors. In a gradient-type optimization algorithm, a positive gradient value pushes the value of g(x) downwards; a negative gradient value pushes the value of g(x) upwards; a gradient value of 0 means that no changes are made. Therefore, the TV prior encourages a monotonic function, suppresses oscillations, and preserves the sharp edges.

As illustrated in FIG. 8, the embodiment performs on the projection data the Edge-preserving FBP-MAP algorithm according to the current invention. For one set of parameters, $\beta$ is set to zero as designated as $\beta_0$ for one noise weighted ramp filter. Referring back to Equation (12), $\beta_0 g(X)$ is zero and no smoothing is enforced at all. Subsequently, the reconstructed image $X_0$ is generated with no smoothing. On the other hand, for the other set of parameters, $\beta$ is set to non-zero as designated as $\beta$ for the other noise weighted ramp filter and the reconstructed image $X_\beta$ is generated with certain amount of smoothing. Thus, two exemplary images $X_\beta$ and $X_0$, are reconstructed where a first image $X_\beta$ is based upon the rFBP-MAP reconstruction with a non-zero $\beta$ value and a second image $X_0$ is based upon the rFBP reconstruction with a zero $\beta$ value.

Figure 9:
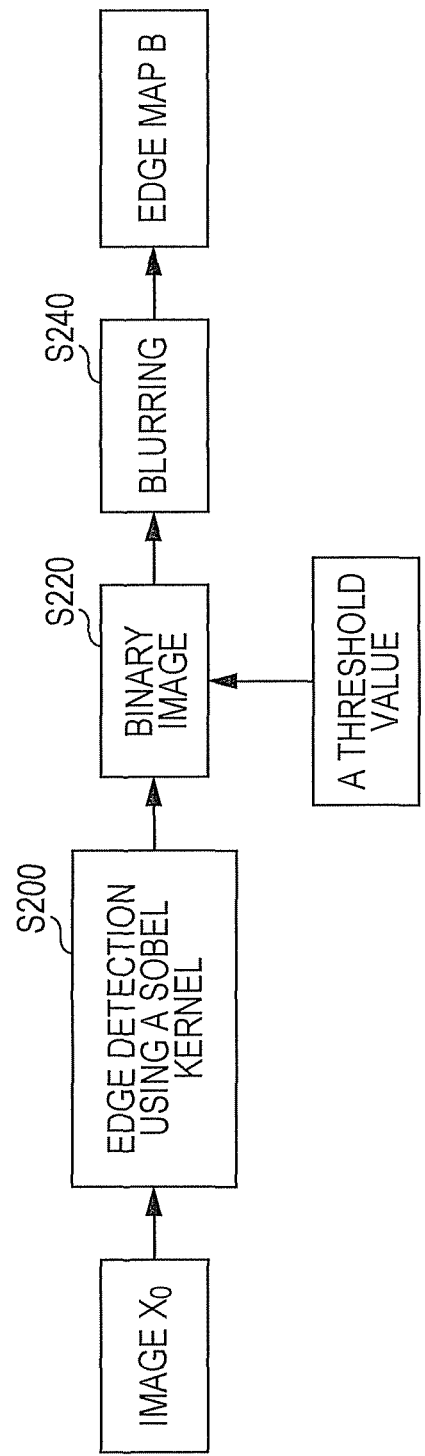
FIG. 9 depicts how an edge map B is generated in one exemplary process according to the current invention.

Now referring to FIG. 9, an edge map B as used in the embodiment as illustrated in FIG. 8 is generated in one exemplary process according to the current invention. One exemplary image $X_0$ is the rFBP reconstruction with a zero $\beta$ value. In exemplary method, the jump is evaluated in a step S200 by edge detection using the well-known Sobel kernel, which is essentially the norm of the image gradient.

The edge image generated by the Sobel kernel is then converted in a step S220 into a binary image with values 0 or 1 according to a predetermined threshold. That is, image values above the threshold are set to 1 while image values below the threshold are set to 0. Subsequently, the binary edge image is blurred in a step S240 by a predetermined low-pass filter, and the resulting blurred image is denoted as B. The motivation for blurring the edge image is to provide a smooth transition between the edge regions and non-edge regions. The final reconstruction is a linear combination of $X_b$ and $X_0$:

$$X = B.*X_0 + (1-B).*X_\beta \quad (13)$$

where .* is the point-wise multiplication as defined in MATLAB®.

Figure 10:
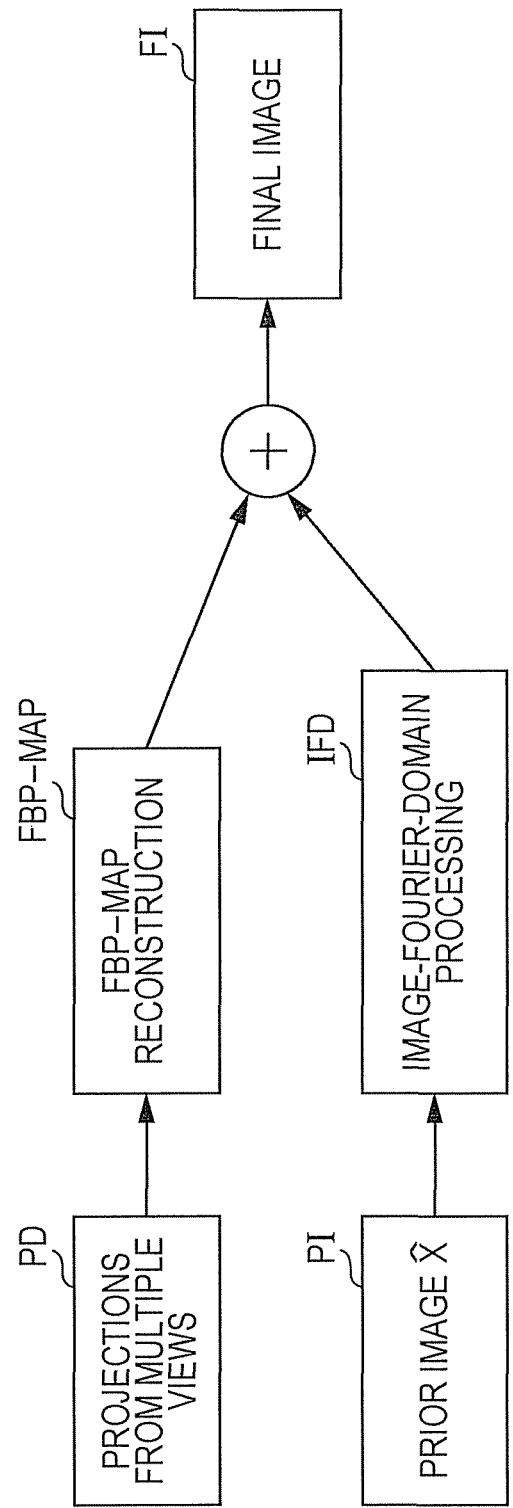
FIG. 10 is a diagram illustrating an exemplary process of reconstructing an image based upon an FBP-MAP algorithm using a predetermined prior image according to the current invention.

Now referring to FIG. 10, a diagram illustrates an exemplary process of reconstructing an image based upon an FBP-MAP algorithm using a predetermined prior image according to the current invention. In general, the objective function (8) is made more general for reconstructing an image based upon an FBP-MAP algorithm by adding a given prior image $\hat{X}$:

$$F = \|P - AX\|_W^2 + \beta_1 X^T R_1 X + \beta_2 (X - \hat{X})^T R_2 (X - \hat{X}). \quad (14)$$

An iterative intermediate solution is expressed by $$X^{(k)} = \{I - [I - \alpha(A^T W A + \beta_1 R_1 + \beta_2 R_2)]^k\} \quad (15)$$
$$(A^T W A + \beta_1 R_1 + \beta_2 R_2)^{-1} (A^T W P + \beta_2 R_2 \hat{X})$$
$$= \{I - [I - \alpha(A^T W A + \beta_1 R_1 + \beta_2 R_2)]^k\}$$
$$[I + (A^T W A)^{-1} (\beta_1 R_1 + \beta_2 R_2)]^{-1} [A^{-1} P + \beta_2 (A^T W A)^{-1} R_2 \hat{X}].$$

An equivalent FBP-MAP algorithm has two Fourier domain filter functions $$H^{1D}_{k,\beta_1,\beta_2,w}(\omega) = \frac{1 - \left(1 - \frac{\alpha w}{|\omega|} - \alpha\beta_1 L_1^{1D} - \alpha\beta_2 L_2^{1D}\right)^k}{1 + \frac{|\omega|}{w}(\beta_1 L_1^{1D} + \beta_2 L_2^{1D})} |\omega|, \quad (16)$$

with
$\omega \neq 0$;

$$G^{2D}_{k,\beta_1,\beta_2,w}(\vec{\omega}) = \frac{1 - \left(1 - \frac{\alpha w}{|\vec{\omega}|} - \alpha\beta_1 L_1^{2D} - \alpha\beta_2 L_2^{2D}\right)^k}{1 + \frac{|\vec{\omega}|}{w}(\beta_1 L_1^{2D} + \beta_2 L_2^{2D})} \beta_2 \frac{|\vec{\omega}|}{w} L_2^{2D}, \quad (17)$$

with
$\vec{\omega} \neq \vec{0}$.

Still referring to FIG. 10, the FBP-MAP algorithm has two inputs including the projections data PD and the prior image PI. The final reconstruction image TRFI is the summation of two components including a first image from the projection data PD and a second image from the prior image PI. An FBP-MAP reconstruction generates the first reconstructed image using the detector-Fourier-domain filter as express in Equation (16) followed by a backprojector. An image-Fourier-domain processing IFD generates a second image using the image-Fourier-domain filter as express in Equation (17). The image-Fourier-domain filter is either 2D or 3D.

Figure 11:
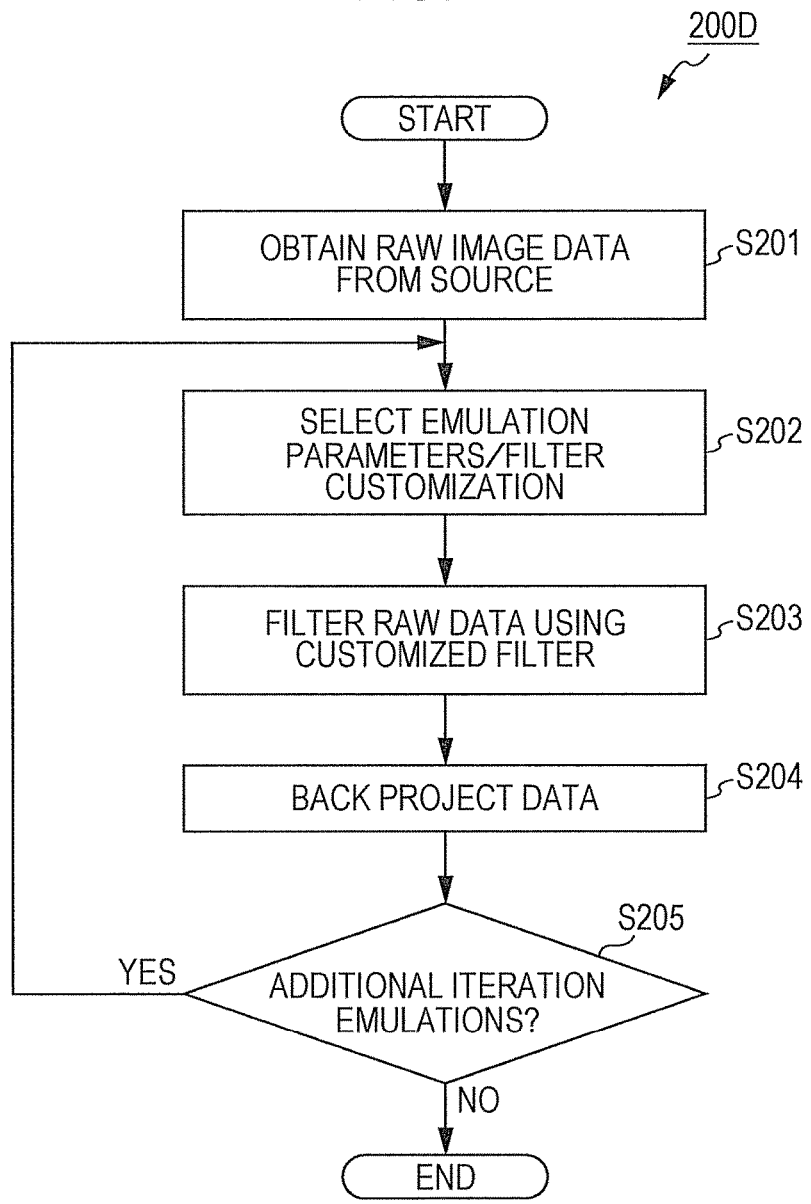
FIG. 11 is a flow chart illustrating steps involved in the process of reconstructing an image with the noise-weighted iteration-emulating FBP algorithm according to the current invention.

Now referring to FIG. 11, a flow chart illustrates steps involved in the process of reconstructing an image with the noise-weighted iteration-emulating FBP algorithm according to the current invention. In general, a reconstruction filter emulates a specific iteration result at a predetermined number of iterations while the reconstruction filter is shaped based upon parameters including the weight value according to a predetermined iterative reconstruction algorithm. An exemplary process of the noise-weighted iteration-emulating FBP algorithm 200D begins by acquiring raw data or projection data from an image source in a step S201. In one embodiment, data is received in the form of a Radon Transform representing line integrals of the object being imaged. In another data, projection data is acquired in any modality such as a CT apparatus as illustrated in FIG. 1 as well as a PET apparatus, a SPECT device and the like.

At least one reconstruction filter is customized or shaped based upon a combination of parameters including but not limited to an iteration number, a noise weight value, a system matrix and so on in a step S202. These parameters are optionally selected to ultimately provide a desired image. For example, a parameter k is selected to emulate a specific iteration result at a predetermined number of iterations according to a predetermined iterative reconstruction algorithm. In addition, a previously determined weight value W is also used in conjunction with the iteration parameter k to shape the reconstruction filter to be applied to the projection data in one embodiment according to the current invention. Other filter parameters include the step size in the iterative algorithm and the relative weighting of the Bayesian term so as to accommodate various applications.

After the reconstruction filter is customized in the step S202 to a desired setting according to a combination of the parameters, the projection data is filtered in a step S203 by applying the customized filter. The filtered data is then backprojected in a step S204 to render an image. The exemplary process determines whether or not it is desirable repeat the iterative emulation in a step S205. If the additional emulation is desired, the exemplary process proceeds to the step S202 fur additional iterative emulation. On the other hand, if the additional emulation is not desired, the exemplary process proceeds to terminate.

Figure 12:
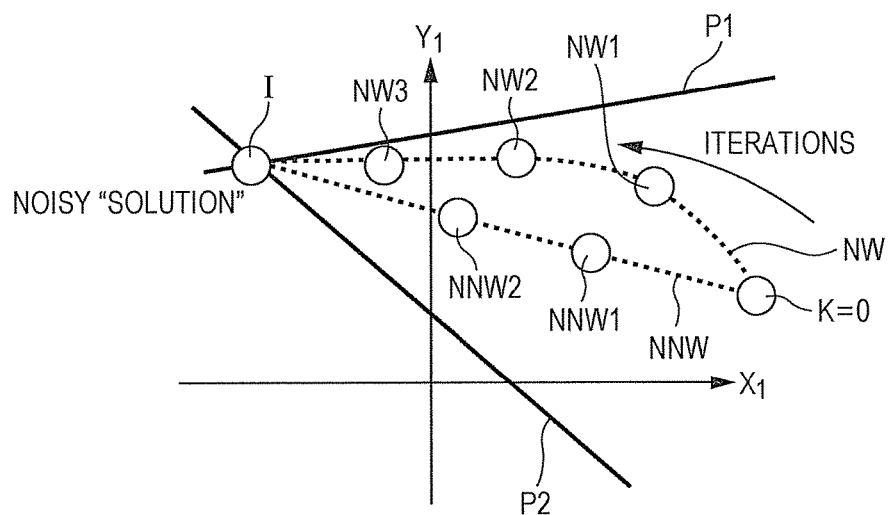
FIG. 12 is a diagram conceptually illustrating the effect of the above described emulated iteration in the noise weighted FBP algorithm according to the current invention.

FIG. 12 is a diagram conceptually illustrating the effect of the above described emulated iteration in the noise weighted FBP algorithm according to the current invention. In prior art CT imaging, noise control has been achieved using either pre-filtering or post-filtering. In contrast, noise is substantially reduced during the image reconstruction using the noise weighted and iteration emulated FBP algorithm according to the current invention. In general, noise reduction in image reconstruction is based on the concept that image reconstruction (especially the backprojection) is a summation procedure and introduction of proper weighting for the projections can reduce the variance of the backprojection.

Still referring to FIG. 12, two projections or measured data are represented by two straight lines P1 and P2, and the solution or the image I is the intersection of the two projection lines P1 and P2. The horizontal axis $X_1$ and the vertical axis $Y_1$ represent two variables in the image I. If one measurement is made from the image, the two image pixels can take values anywhere along one straight line. If two independent measurements are made, the values of the two image pixels are determined, which is the intersection of the two straight lines. If a third measurement is made, and all measurements contain noise, the three straight lines may not intersect at one point. In general, when the image consists of many pixels and many inconsistent noisy measurements are made, a solution of the imaging problem may not exist because the measurements may not meet at a single point.

In mathematics, if the noisy measurements are inconsistent, the measurements are referred to as "not in the range of the projection operator." On the other hand, if the measurements are consistent, they are mapped into a range of the projection operator. In fact, the mapping is guaranteed by the backprojector in an FBP algorithm because only data components in the range of the projector are backprojected into the image domain. In other words, the projection inconsistency has no contribution to the FBP reconstructed images. Without loss of generality, it can be assumed that the situation as illustrated by a strait line, where the measurements are consistent but still noisy and in the range of the projection operator even for an image with many pixels. Unlike an iterative algorithm, the FBP algorithm is able to provide a unique but noisy solution from a set of noisy projections.

Still referring to FIG. 12, in order to produce a less noisy image, the FBP algorithm is modified to emulate a plurality of iterative steps of the iterative algorithm. A solution trajectory is illustrated from the initial value at k=0 towards the ultimate solution at k=∞. Although a subsequent iteration of the FBP algorithm moves the resultant image with less noise, the iterative algorithm is usually stopped before the true solution is reached. This is particularly true if the true solution is noisy because the measured data contains noise due to low photon counts.

One solution trajectory from k=0 is a straight line towards the true solution or the image I, and the straight line indicates that the emulated iterations are not weighted by noise variance. The points NNW1 and NNW2 on a straight line indicate intermediate results respectively after a first predetermined number of iterations and a second predetermined number of iterations. In this example, the second number of iterations is larger than the first number of iterations, and the intermediate result NNW2 is emulated after the second number of iterations. On the other hand, the intermediate results NW1, NW2 and NW3 are located on a curved line, and the curved line indicates that the emulated iterations are weighted by noise variance. The intermediate results NW1, NW2 and NW3 are respectively after a third predetermined number, a fourth predetermined number and a fifth predetermined number of iterations. In the example, the fifth number is larger than the third and fourth numbers of iterations, and the third number is the smallest. The intermediate result NW3 is emulated after the fifth number of iterations. The solution trajectory is determined by a set of weighting factors. One weighting factor is assigned to each measurement. A larger factor implies that the associated measurement is more trustworthy. A common approach is to assign the weighting factor that is proportional to the reciprocal of the noise variance of the measurement.

A less noisy pseudo solution in the neighborhood of the true noisy solution is accepted in practice. A sequence of pseudo solutions is parameterized by a predetermined set of parameters including a noise variance weight value and an iteration index k. In general, a pseudo solution with a smaller k corresponds to a smoother image while a pseudo solution with a larger k corresponds to a sharper image but noisier.

In the following, additional embodiments are described with respect to a specific combination of the above features according to the current invention. One embodiment utilizes a ray-by-ray noise weighted FBP with maximum a posteriori (MAP) algorithm, which is designated by rFBP-MAP. The derivation steps for the rFBP-MAP algorithm are very similar to those for the view-by-view weighted FBP-MAP algorithm. Some major derivation steps are briefly given below. An objective function is the same as Equation (12). If the Bayesian term g(X) is quadratic, the gradient of g(X) is in the form of RX for some matrix R, and the solution can be obtained by the Landweber algorithm:

$$X^{(k+1)} = X^{(k)} + \alpha[A^T W(P - AX^{(k)}) - \beta RX^{(k)}] \tag{18}$$

The recursive expression of Equation (18) has an equivalent non-recursive expression. When the initial condition is zero, the non-recursive expression is:

$$X^{(k+1)} = \left[\sum_{n=0}^{k} (I - \alpha A^T WA - \alpha \beta R)^n\right] \alpha A^T WP \tag{19}$$

If $(A^T WA + \beta R)^{-1}$ exists, the summation in (19) has a closed-form as $$X^{(k)} = [I - (I - \alpha A^T WA - \alpha \beta R)^k](A^T WA + \beta R)^{-1} A^T WP \tag{20}$$

If $(A^T WA)^{-1}$ exist, $(A^T WA + \beta R)^{-1} = [I + \beta(A^T WA)^{-1} R]^{-1} (A^T WA)^{-1}$. If it is further assumed that sufficient sampling leads to the existence of Radon inversion $A^{-1}$, then it leads to $(A^T WA)^{-1} = A^{-1} W^{-1} (A^T)^{-1}$ and $(A^T WA)^{-1} A^T W = A^{-1}$. Therefore, Equation (20) can be reduced to:

$$X^{(k)} = [I - (I - \alpha A^T WA - \alpha \beta R)^k][I + \beta(A^T WA)^{-1} R]^{-1} A^{-1} P \tag{21}$$

If $A^{-1}$ does not exist for a reason such as an insufficient number of views, one can verify that the FBP algorithm is a pseudo-inverse of the projection operator A and $(A^T WA)^+ A^T W = A^+$, where "+" denotes the pseudo-inverse and $A^+$ is ramp filtering followed by backprojection $A^T$. Thus, Equation (21) still holds with the inverse "−1" by replacing the pseudo-inverse "+". Hereafter, we will not distinguish the inverse and the pseudo-inverse. The notation "$A^{-1}P$" will be used to represent the conventional FBP reconstruction.

In Equation (21), $[I - (I - \alpha A^T WA - \alpha \beta R)^k]$ represents the windowing effect at the kth iteration of the iterative algorithm and becomes the identity matrix as k tends to infinity, and $[I + \beta(A^T WA)^{-1} R]^{-1}$ represents the effect of the Bayesian regularization. When β=0, the Bayesian modification is not effective. Expression (21) provides insights and understanding of how an iterative algorithm handles the noise-weighting and Bayesian regularization, and it can also lead to develop an FBP-type algorithm to perform the same tasks.

Lastly, a Fourier domain expression is derived from the matrix expression so that an FBP-type algorithm is obtained. The matrix $A^{-1}$ is treated as 1D ramp filtering followed by backprojection or backprojection followed by 2D ramp-filtering. When the matrix expression (21) is viewed as a "backproject first, then filter" algorithm, the image domain filtering in Equation (21) is implemented in the 2D Fourier domain with a transfer function of $$H^{2D}_{k,\beta,w}(v_x, v_y) = \frac{1 - \left(1 - \frac{\alpha w}{\|\vec{v}\|} - \alpha \beta L^{2D}\right)^k}{1 + \beta \frac{\|\vec{v}\|}{w} L^{2D}} \|\vec{v}\|, \tag{22}$$

with $$\|\vec{v}\| = \sqrt{v_x^2 + v_y^2} \neq 0$$

where $v_x$ and $v_y$ are the frequencies respectively with respect to x and y, and $\vec{v} = (v_x, v_y)$ is the 2D frequency vector. When $\|\vec{v}\| = 0$, we define $H^{2D}_{k,\beta,w}(0,0) = 0$. As known, if the projection operator A is the line-integral (i.e., the Radon transform) in the 2D space and $A^T$ is the operator (i.e., the backprojection transform), the combined operator of projection-and-backprojection, $A^T A$, is the 2D convolution of the original image with a 2D kernel $1/r$, where $r=\sqrt{x^2+y^2}$ in the x-y Cartesian coordinates. The 2D Fourier transform of $1/r$ is $1/\|\vec{v}\|$. In Equation (22), the Fourier domain equivalence of R is denoted by $L^{2D}$.

By using the central slice theorem, image domain 2D filtering is converted into projection domain 1D filtering. The 2D image Fourier domain transfer function (22) is equivalent to the 1D projection Fourier domain transfer function:

$$H^{1D}_{k,\beta,w}(\omega) = \frac{1 - \left(1 - \frac{\alpha w}{|\omega|} - \alpha \beta L^{1D}\right)^k}{1 + \beta \frac{|\omega|}{w} L^{1D}} |\omega|, \quad (23)$$

with $$\omega \neq 0$$

where $\omega$ is the frequency with respect to the variable along the detector. When $\omega=0$, we define $H_{k,\beta,w}^{1D}(0)=0$. In Equation (23), $L^{1D}$ is the central slice of $L^{2D}$ of Equation (22). In this new rFBP-MAP algorithm, $H_{k,\beta,w}^{1D}(\omega)$ is the modified ramp filter expressed in the 1D Fourier domain. The iteration effect is characterized by $$\left(1 - \frac{\alpha w}{|\omega|} - \alpha \beta L^{1D}\right)^k$$

and the Bayesian effect is characterized by $$\beta \frac{|\omega|}{w} L^{1D}.$$

The ultimate ($k=\infty$) solution does not depend on the noise-weighting w if $\beta=0$, but it depends on the noise-weighting w if $\beta \neq 0$. No modification is required for the backprojector for the new rFBP-MAP algorithm.

The noise-dependent weighting factor w in Equations (22) and (23) is not a constant. For the view-based noise weighting, w is a function of the view angle: w=w(view). For the ray-based noise weighting, w is a function of the ray: w=w(ray). A popular approach to assign the weighting factor is to let w(ray) be proportional to the reciprocal of the noise variance of the ray measurement. This approach is justified by using the likelihood function (i.e., the joint probability density function) as the objective function for an optimization problem. The philosophy is that we should trust the less noisy measurements more than noisier measurements. When k tends to infinity and β tends to zero, the modified ramp filter (23) becomes a conventional ramp filter and the rFBP-MAP algorithm reduces to the conventional FBP algorithm.

In implementing the rFBP-MAP algorithm, the inverse Fourier transform of $H_{k,\beta,w}^{1D}(\omega)$ is assumed to be $h_{k,\beta,w}^{1D}(t)$, which is the spatial-domain kernel of the 1D modified ramp filter. In the rFBP-MAP algorithm, since w is a function of the projection ray, w=w(t, θ). Let p(t, θ) be the projection at view θ and location t on the detector, and q(t, θ) be the filtered projection. Then q(t, θ) is defined by the following integral:

$$q(t, \theta) = \int_{-\infty}^{\infty} p(\tau, \theta) h^{1D}_{k,\beta,w(t,\theta)}(t-\tau) d\tau, \quad (24)$$

which is not a convolution because the kernel $h_{k,\beta,w(t,\theta)}^{1D}(\tau)$ depends on θ and t. If the filtering procedure is implemented in the spatial domain as in Equation (24), the calculation cost is the same as convolution. Therefore, the rFBP-MAP algorithm is computationally efficient. The easiest and most efficient way to implement the proposed rFBP-MAP algorithm is to use (24) to filter the projections in the spatial domain.

Currently, there is no analytical expression for the integration kernel $h_{k,\beta,w}^{1D}(t)$. An alternative way to calculate q(t, θ) is to implement Equation (24) at each view angle θ in the frequency domain as follows.

Step 1: Find the 1D Fourier transform of p(t, θ) with respect to t, obtaining P(ω, θ).

Step 2: For each ray t, assign a weighting factor w(t) and form a frequency domain transfer function (23). In implementation, ω is a discrete frequency index and takes the integer values of 0, 1, 2, . . . and so on.

Step 3: Find the product: $Q_t(\omega, \theta) = P(\omega, \theta) H_{k,\beta,w(t,\theta)}^{1D}(\omega)$.

Step 4: Find the 1D inverse Fourier transform of $Q_t(\omega, \theta)$ with respect to □, obtaining q(t, θ).

Step 1 processes all t's in each view while Steps 2 through 4 process only one t at a time.

The above described rFBP-MAP algorithm is not restricted to the parallel-beam imaging geometry. It is optionally extended to other imaging geometries including fan-beam, cone-beam, planar-integrals and attenuated measurements as long as an FBP algorithm exists. The only modification to the FBP algorithm is in projection data filtering. Each measurement is assigned a weighting factor, and a frequency-domain filter transfer function is formed as (23), which is imaging geometry independent.

To illustrate the effects of the rFBP-MAP algorithm, a cadaver torso was scanned using an X-ray CT scanner using a low-dose setting, and the images were reconstructed with a conventional FBP (the Feldkamp) algorithm as well as the rFBP-MAP algorithm. The imaging geometry was cone-beam, the X-ray source trajectory was a circle of radius 600 mm. The detector had 64 rows, the row-height was 0.5 mm, each row had 896 channels, and the fan angle was 49.2°. The tube voltage was 120 kV and current was 60 mA. There were 1200 views uniformly sampled over 360°.

Using the Feldkamp algorithm as an FBP algorithm, the data were first weighted with a cosine function, then a 1D ramp filter was applied to each row of the cone-beam projections. Finally a cone-beam backprojection was used to generate a 3D image volume. For the implementation of the rFBP-MAP algorithm, the 1D ramp filter was replaced by the ramp filter as expressed in Equation (23). The iteration index k was chosen as 20,000, and the step-size α was set to 2.0. For an edge-preserved MAP reconstruction two β values were used: β=0.0005 and β=0. The Bayesian penalty function g(X) was the common quadratic function of the difference between the central pixel value and the average value of its four neighbors in its transaxial slice. In other words, R was simply a Laplacian, whose 1D version was a second order derivative with a kernel of [−1 2 −1]. The noise weighting function was defined by w(t,θ)=exp(−p(t,θ)), in which we assumed that the transmission measurement was approximately Poisson distributed and the line-integral p(t, θ) was the logarithm of the transmission measurement.

The edge map image was obtained in a slice-by-slice manner, using the 2D Sobel kernel. The edge detection threshold was set at the 70% of the maximum image value. A 3×3 smooth kernel was then used to blur the binary edge image to obtain the image B to be used in Equation (13).

The image volume was reconstructed in a 512×512×512 3D array, and a non-central axial slice is used for display. No other pre-filtering or post-filtering was applied to the reconstruction.

Figure 13A:
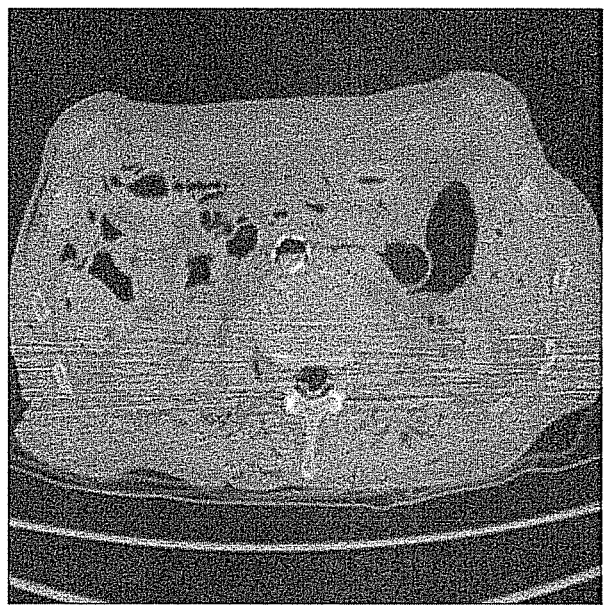
FIG. 13A is a reconstructed image based upon the conventional FBP Feldkamp algorithm for a transverse slice in the abdominal region of the cadaver.
Figure 13B:
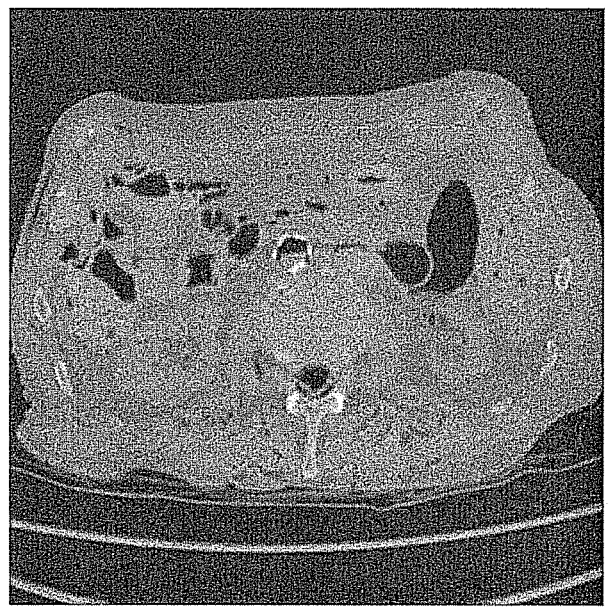
FIG. 13B shows a reconstruction image, which is the rFBP-MAP reconstruction with $\beta=0$.
Figure 13C:
FIG. 13C shows the rFBP-MAP reconstruction with $\beta=0.0005$, using a quadratic smoothing prior.
Figure 13D:
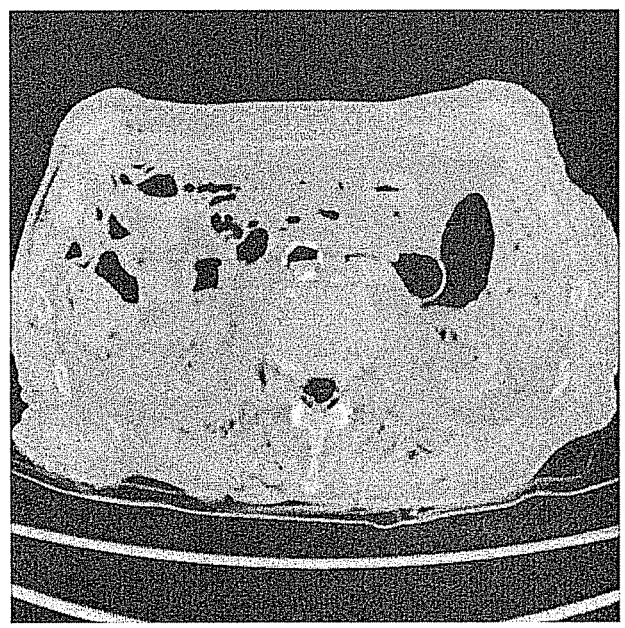
FIG. 13D shows the rFBP-MAP reconstruction with edge preserved prior, which is essentially the weighted combination of FIG. 13B and FIG. 13C.
Figure 13E:
FIG. 13E shows the edge map B used for edge-preserving FBP-MAP reconstruction.

Now referring to FIG. 13A, an image is reconstructed based upon the conventional FBP Feldkamp algorithm for a transverse slice in the abdominal region of the cadaver. Due to the low dose, severe streaking artifacts from left-to-right across the torso are evident. FIG. 13B shows the rFBP reconstruction, which is the rFBP-MAP reconstruction with β=0. The ray-based noise weighting in the rFBP algorithm effectively removed the streaking artifacts that appear in FIG. 13A. FIG. 13C shows the rFBP-MAP reconstruction with β=0.0005, using a quadratic smoothing prior. Due to the noise weighting, the streaking artifacts are gone. Because of the blurring prior, the reconstruction looks over-smoothed especially in the edge regions. FIG. 13D shows the rFBP-MAP reconstruction with edge preserved prior, which is essentially the weighted combination of FIG. 13B and FIG. 13C. The combination weighting image B was extracted form $X_0$ with an edge detection Sobel kernel. The edge image was binary. A lowpass filter was used to blur the edge image so that the transition from edge regions to non-edge regions was smooth. The image in FIG. 13D is less noisy than FIG. 13B but maintains the main edges in FIG. 13B un-smoothed. FIG. 13E shows the edge map B used for edge-preserving FBP-MAP reconstruction.

Figure 13F:
FIG. 13F is vFBP-MAP reconstruction.

In order to improve the computation efficiency, the view-based noise weighting vFBP-MAP algorithm can be used for many applications. The noise weighting can be determined by the largest noise variance at each projection view. A vFBP-MAP reconstruction is shown in FIG. 13F, in which all parameters are the same as in the reconstruction of FIG. 13D except the noise weighting function w.

In one embodiment of the image reconstructing device according to the current invention, the noise model includes Poisson statistics or the noise model is described by a compound Poisson statistics of photon intensity measurements with Gaussian distributed electronic noise. In probability theory, a compound Poisson distribution is the probability distribution of the sum of independent identically-distributed random variables, where the number of variables follows the Poisson distribution. Poisson distribution is well suited to describe the number of incident photons. Denote by N, the number of photons hitting the detector during the integration time is N~Poisson(λ), where λ is the count rate. Each detected photon has a random energy $X_i$, whose distribution is described by the x-ray tube polychromatic spectra and detector efficiency. Assuming an energy integrating detector, the deposited energy is given by $Y=\Sigma_N X_i$. It follows that deposited energy Y follows the compound Poisson statistics (mean value and variance):

$$E[Y]=E[N]E[X], \quad (25)$$

$$\mathrm{Var}[Y]=E[N]E[X^2]=E[N](E[X]^2+\mathrm{Var}[X]) \quad (26)$$

A concept of variance gain is denoted by W and defined as follows:

$$W=\mathrm{Var}[Y]/E[Y]. \quad (27)$$

Note that for a Poisson distributed random variable W=1. For the compound Poisson variable we have:

$$W=E[X]+\mathrm{Var}[X]/E[X]. \quad (28)$$

Thus, noise variance gain is proportional to the mean effective energy of the spectra incident onto the detector. In general, there are several factors affecting mean spectrum energy:
1) Tube potential (kVp). Typically it varies from 80 to 140 kVp, and determines the high limit of spectrum energy.
2) Bowtie and spectrum filtration, heel effect. These are always present in CT data. Due to bowtie and heel effect, spectra is different for each detector pixel, and therefore calculations need to be done for each detector pixel independently.
3) Object size and composition. It is a well known effect that objects harden the beam, i.e., increase E[X], and beam hardening depends on path-length and attenuation.

The effect of mean spectrum energy on the noise variance gain is used for a compound Poisson model. Acquired data are given by:

$$Z=gY+e, \quad (29)$$

where g is a detector gain factor, and e is the electronic noise with variance $V_e$. To measure $V_e$ we collect data with x-ray tube switched off and measure the variance. The mean and variance are measured in time direction for each detector pixel independently. Statistics of the acquired data is given by:

$$E[Z]=gE[Y], \mathrm{Var}[Z]=g^2\mathrm{Var}[Y]+V_e. \quad (30)$$

It can be shown that $$gW=(\mathrm{Var}[Z]-V_e)/E[Z]. \quad (31)$$

After collecting object data we can measure mean E[Z] and variance Var[Z] and compute gW. Note that gain g cannot be easily obtained from the raw data; to compensate the effect of unknown scale g, we calibrate the raw data by air scan data ($W_{OBJ}=W/W_{AIR}$). The proposed compound Poisson model of noise variance can be written as:

$$\mathrm{Var}[Z]=V_e+gWE[Z], \quad (32)$$

where W is given by Equation (28).

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of reconstructing an image, comprising:
   determining a weight value for weighing projection data at least according to a predetermined noise model;
   dynamically shaping at least one windowed frequency-dependent reconstruction filter based upon parameters including the weight value, wherein the windowed frequency-dependent reconstruction filter including integration kernel;
   regularizing to shape the windowed frequency-dependent reconstruction filter, and
   generating an image based upon the windowed frequency-dependent reconstruction filter, wherein an additional one of the windowed frequency-dependent reconstruction filter is provided and the two of the windowed frequency-dependent reconstruction filters are shaped for being respectively applied to generate a first image for preserving edges and a second image for reducing noise, generating an edge map, the image is generated based upon the first image, the second image and the edge map.

2. The method of reconstructing an image according to claim 1 wherein the weight value is determined based upon views in the projection data.

3. The method of reconstructing an image according to claim 1 wherein the weight value is determined based upon rays in the projection data.

4. The method of reconstructing an image according to claim 1 wherein the windowed frequency-dependent reconstruction filter is applied to the projection data before backprojection is performed.

5. The method of reconstructing an image according to claim 1 wherein the windowed frequency-dependent reconstruction filter is applied to the projection data after backprojection is performed.

6. The method of reconstructing an image according to claim 1 wherein the noise model includes Poisson statistics.

7. The method of reconstructing an image according to claim 1 whereas the noise model is described by a compound Poisson statistics of photon intensity measurements with Gaussian distributed electronic noise.

8. The method of reconstructing an image according to claim 1 wherein the image is generated additionally based upon a reference image.

9. The method of reconstructing an image according to claim 1 wherein the windowed frequency-dependent reconstruction filter is shaped to emulate a specific iteration result at a predetermined number of iterations according to a predetermined iterative reconstruction algorithm.

10. The method of reconstructing an image according to claim 9 wherein the system matrix specifies non-uniform sampling of the projection data.

11. The method of reconstructing an image according to claim 1 wherein the windowed frequency-dependent reconstruction filter is shaped based upon a system matrix.

12. A system for reconstructing an image, comprising:
a noise weight determining circuit for determining a weight value for weighing projection data at least according to a predetermined noise model;
a filter shaping circuit connected to said noise weight determining circuit for dynamically shaping at least one windowed frequency-dependent reconstruction filter based upon parameters including the weight value, wherein the windowed frequency-dependent reconstruction filter including integration kernel;
a regularizing circuit for regularizing to shape the windowed frequency-dependent reconstruction filter; and
an image generating circuit connected to said filter shaping circuit for generating an image based upon the windowed frequency-dependent reconstruction filter, wherein an additional one of the windowed frequency-dependent reconstruction filter is provided and said filter shaping circuit shapes the two of the windowed frequency-dependent reconstruction filters for being respectively applied to generate a first image for preserving edges and a second image for reducing noise, generating an edge map, the image is generated based upon the first image, the second image and the edge map.

13. The system for reconstructing an image according to claim 12 wherein said noise weight determining circuit determines the weight value based upon views in the projection data.

14. The system for reconstructing an image according to claim 12 wherein said noise weight determining circuit determines the weight value based upon rays in the projection data.

15. The system for reconstructing an image according to claim 12 wherein said image generating circuit applies the windowed frequency-dependent reconstruction filter to the projection data before backprojection is performed.

16. The system for reconstructing an image according to claim 12 wherein said image generating circuit applies the windowed frequency-dependent reconstruction filter to the projection data after backprojection is performed.

17. The system for reconstructing an image according to claim 12 wherein the noise model includes Poisson statistics.

18. The system for reconstructing an image according to claim 12 whereas the noise model is described by a compound Poisson statistics of photon intensity measurements with Gaussian distributed electronic noise.

19. The system of reconstructing an image according to claim 12 wherein the image is generated additionally based upon a reference image.

20. The system for reconstructing an image according to claim 12 wherein said filter shaping circuit shapes the windowed frequency-dependent reconstruction filter to emulate a specific iteration result at a predetermined number of iterations according to a predetermined iterative reconstruction algorithm.

21. The system for reconstructing an image according to claim 12 wherein the windowed frequency-dependent reconstruction filter is shaped based upon a system matrix.

22. The system for reconstructing an image according to claim 21 wherein the system matrix specifies non-uniform sampling of the projection data.

* * * * *